Figure 1:
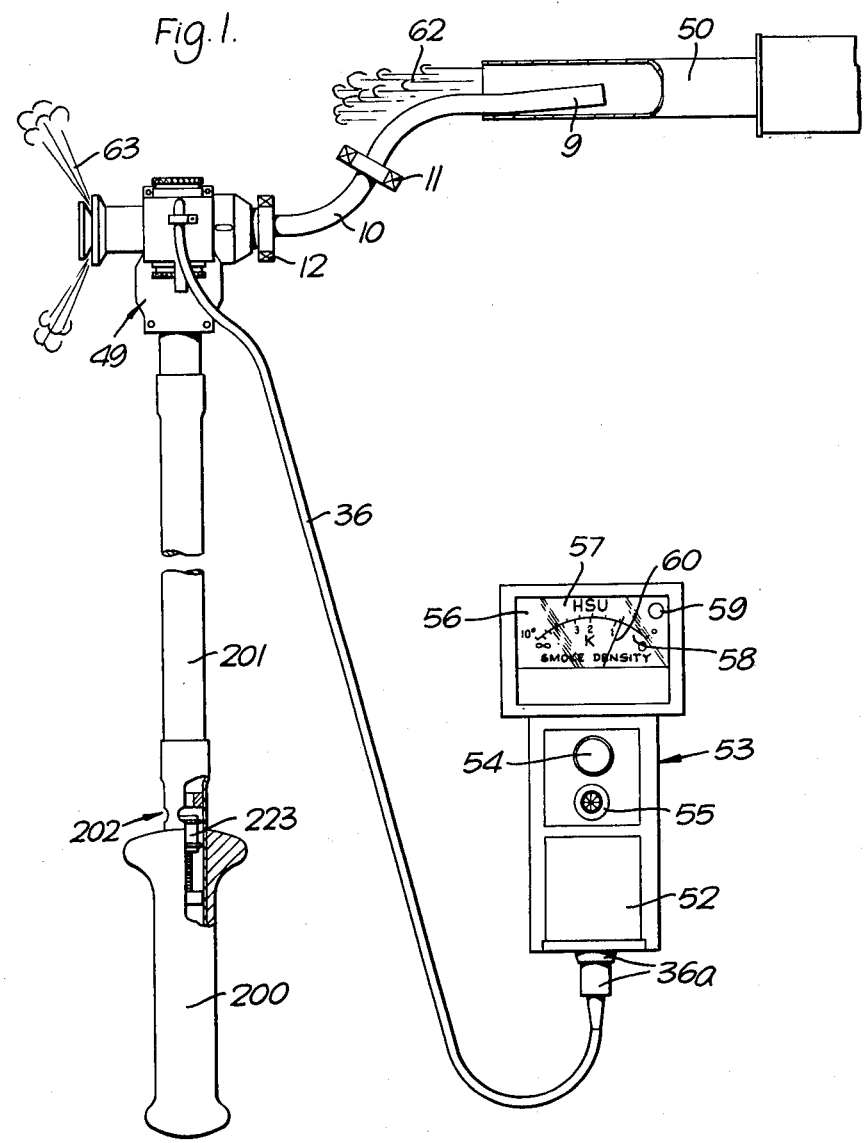

United States Patent [19]

Emerson

[11] 4,066,364
[45] Jan. 3, 1978

[54] APPARATUS FOR MEASURING SMOKE DENSITY

[75] Inventor: Reginald Stanley Emerson, Buckingham, England

[73] Assignee: Leslie Hartridge Limited, England

[21] Appl. No.: 680,084

[22] Filed: Apr. 26, 1976

[30] Foreign Application Priority Data

Apr. 29, 1975 United Kingdom ............... 17848/75

[51] Int. Cl.² ........................................... G01N 21/26
[52] U.S. Cl. ..................................... 356/207; 250/343; 250/576
[58] Field of Search ............... 250/343, 346, 573, 575, 250/576; 356/207

[56] References Cited

U.S. PATENT DOCUMENTS

| 3,496,558 | 2/1970 | Willson et al. | 356/207 |
| 3,816,004 | 6/1974 | Bignardi | 356/207 |
| 3,885,162 | 5/1975 | Geertz | 356/207 |
| 3,932,137 | 1/1976 | Culpepper | 356/207 |
| 3,958,122 | 5/1976 | Jowett et al. | 250/346 |

FOREIGN PATENT DOCUMENTS 168,298    1934    Switzerland ................. 356/207

Primary Examiner—John K. Corbin
Assistant Examiner—Richard A. Rosenberger
Attorney, Agent, or Firm—Berman, Aisenberg & Platt

[57] ABSTRACT

Apparatus for measuring smoke density comprising a venturi passage through which smoke can pass, and a light source and at least one light-reflecting surface arranged in the vicinity of the passage to pass and reflect a light beam transversely through the throat of the venturi to form a V-shaped or multiple V-shaped beam.

14 Claims, 13 Drawing Figures

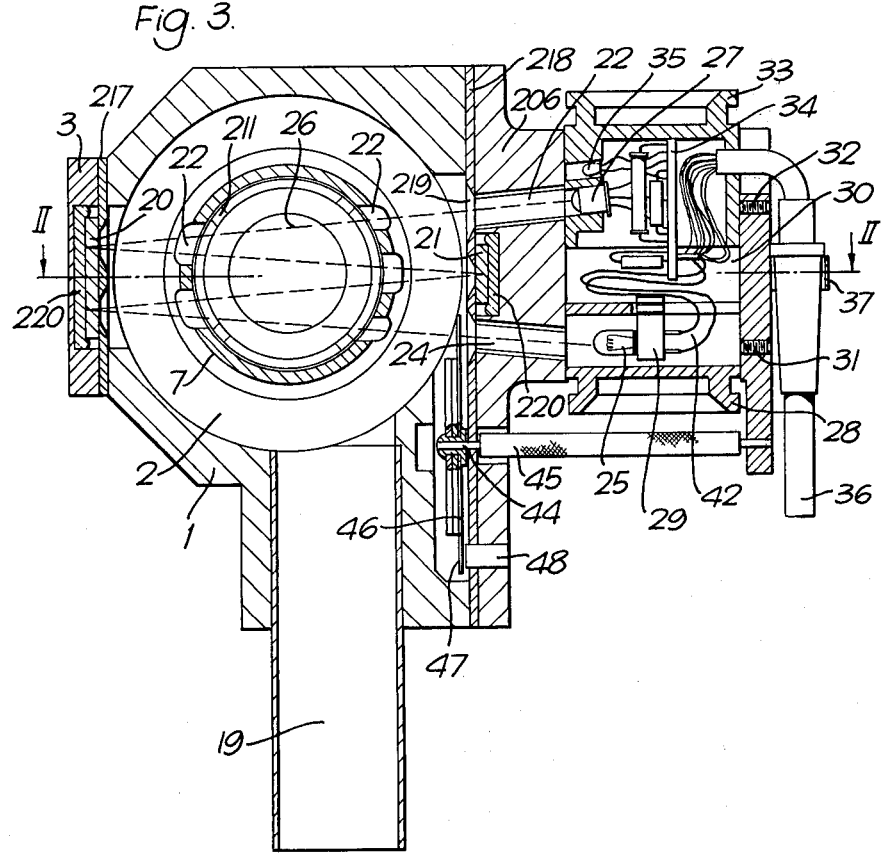
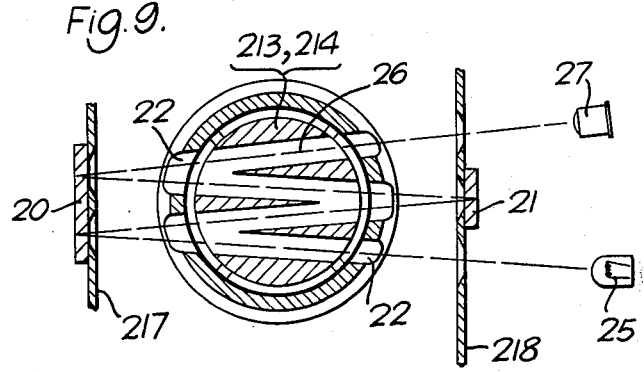

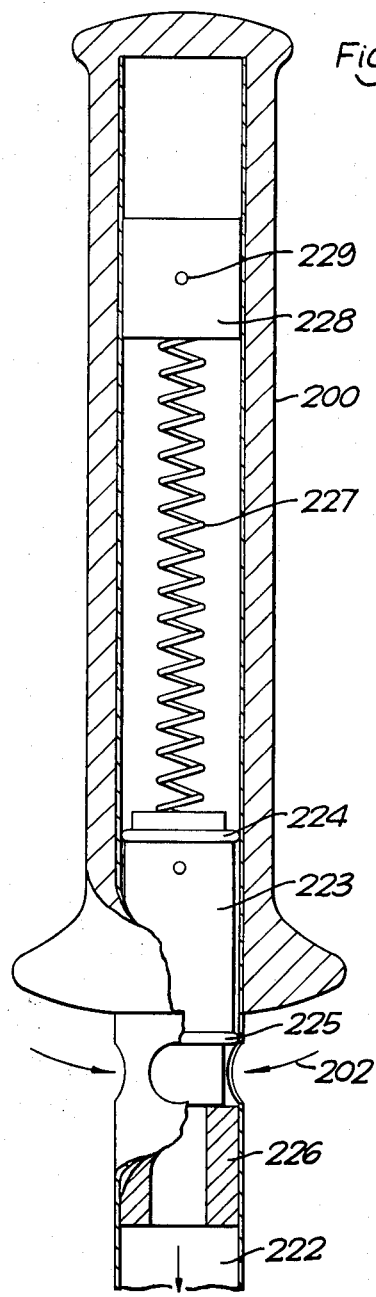
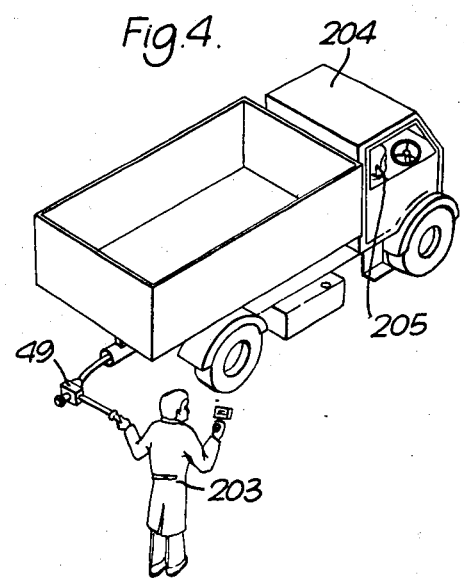

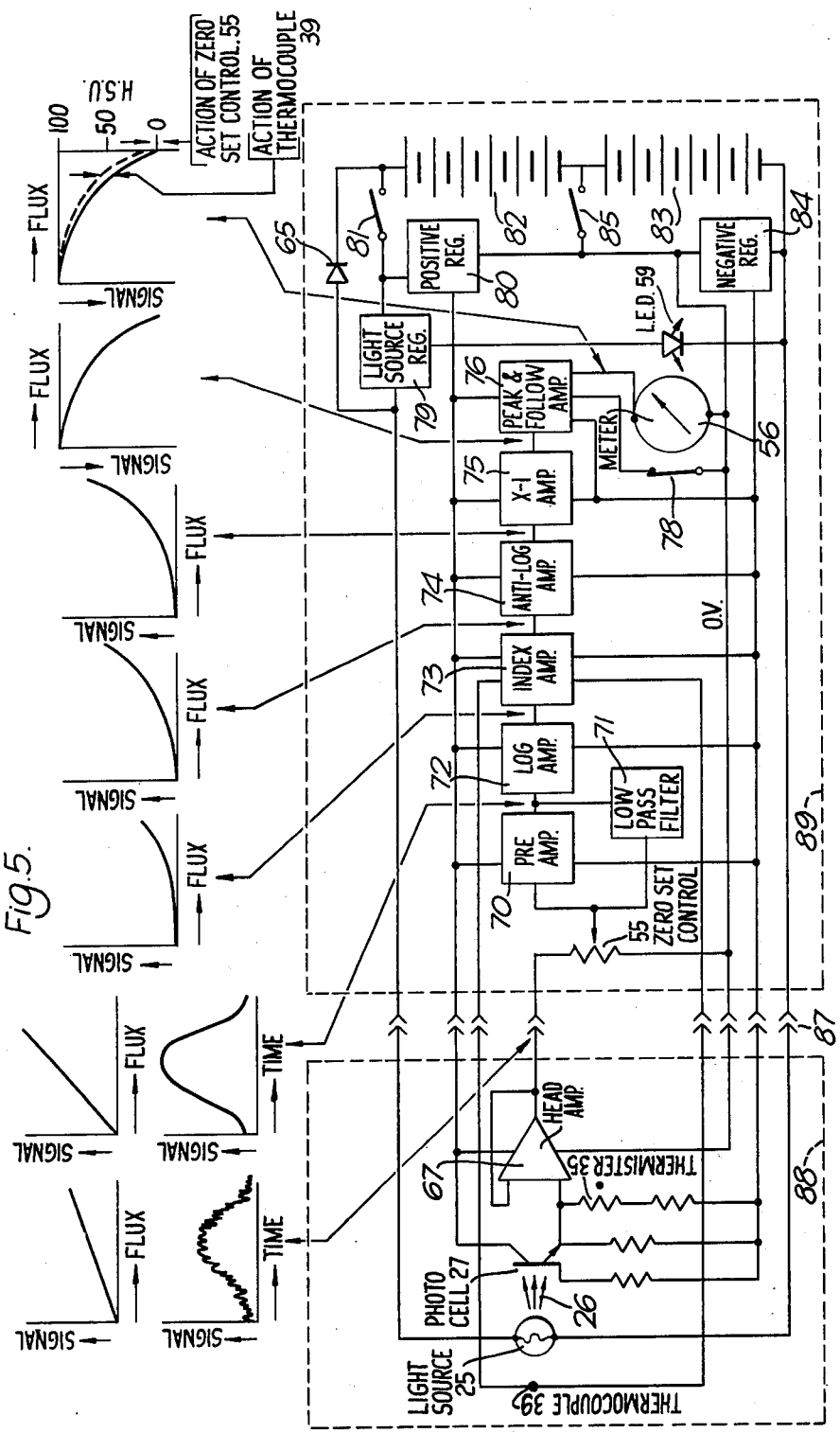

APPARATUS FOR MEASURING SMOKE DENSITY

This invention relates to apparatus for measuring smoke density. It finds particular use in the automotive field for measuring the density of smoke emission from vehicle exhausts, but is equally capable of measuring smoke density from any exhaust pipe or other orifice from which partially opaque gas issues.

Instruments for measuring smoke density are well known and they operate on a number of different principles. The apparatus of the present invention falls into a generic group sometimes referred to as "exhaust opacimeters". These are used mainly for measuring the smoke emission from diesel engines. They operate by causing a beam of light to pass through the gas and to fall on a light-sensitive cell. The output from the cell is then expressed on a suitable display giving a reading of opacity or density. The light beam used may be in the infra red range using a light emitting diode (L.E.D.) rather than a tungsten filament lamp. This permits the light beam to be intermittent (i.e., "chopped") which gives certain advantages in the electronic circuitry.

The whole of the gas volume may pass through an observation chamber (full-flow meter) or only a proportion may be led to the chamber (sampling meter). Full-flow meters may dispense with the observation chamber altogether and pass the light beam directly and transversely through the plume of gas issuing from the exhaust pipe. The meters may be designed for permanent installation in the exhaust pipe or duct through which the gas passes, as for example in an engine test cell. Sampling meters may be provided with a probe of smaller diameter for insertion into the efflux end of the exhaust pipe. In engine test cells, they may utilise a 'T' connection into the exhaust pipe. Similarly, full-flow meters may use a probe of similar diameter to the exhaust pipe and adapted for leakproof attachment to it.

There are several different systems of units in general use for assessing smoke density. Among these are the following:

The expressions "percentage opacity" and "percentage obscuration" mean that, when there is no smoke, the percentage is zero, while when the smoke is infinitely dense (so that the light is completely cut off) the percentage is 100. The scale is then a linear relationship between photo-cell output and meter needle deflection between the extremes.

In order that the above unit may have consistent meaning, the sampling length of the light beam passing through the smoke must be defined. And since smoke expands with temperature and contracts with pressure, these too must be defined. The "Hartridge Smoke Unit" (H.S.U.), which is in wide general use, is a scale of percentage opacity in which the sampling length is defined as 430 mm, the temperature as 100° C., and the pressure as ambient atmospheric pressure.

Meters operating directly across the smoke plume issuing from the exhaust pipe can only define the sampling length in terms of exhaust pipe diameter, and therefore correlation formulae, tables or nomograms are necessary for comparison purposes. Furthermore, temperature cannot be controlled and must either be measured or assumed to be within certain acceptable limits. To provide a common basis, an "Absolute Unit" (K meters$^{-1}$) has been established in which K is a light absorption coefficient according to the formula $$K = \frac{-1}{L} \log_e \left(1 - \frac{N}{100}\right)$$

where L = sampling length in m., and

N = percentage of full scale deflection, K being based on a temperature of 100° C and ambient atmospheric pressure. There is therefore a direct relationship between K and H.S.U., the H.S.U. scale being linear from 0 – 100, and the K scale being non-linear from 0 to ∞.

There are two basic smoke measurements, namely, "steady state measurement" where the engine is under steady load and smoke density can be displayed as a continuous reading, and "dynamic measurement" (or "acceleration measurement") where the engine is installed in a vehicle and steady load cannot conveniently be applied. In this latter case, full load is applied temporarily by using the inherent inertia of the engine itself during a full-throttle free acceleration to full governed speed. Smoke from the exhaust therefore only occurs for a short period while the engine accelerates. The meter must therefore respond sufficiently rapidly to facilitate reading the true maximum smoke density of the short duration (approximately 2 seconds) smoke pulse.

Steady measurements are used in engine development work and vehicle homologation checks. But this type of test, being dependent on a steady known load being applied, is not satisfactory for conformity testing when the vehicle is in use on the road and a chassis dynamometer is not available.

There are a number of criticisms of the acceleration measurement method of test but it is the only method at present available for roadside use and it can be quick and generally satisfactory provided the smoke measurement instrument conforms to the appropriate requirements necessitated by this type of test.

Among the disadvantages of some of the equipment currently used (from the point of view of acceleration smoke measurement) are the following:

1. It requires to be permanently fitted into the exhaust system.
2. Long probe pipes which cause a physical lag and "flattening" of the smoke pulse are needed.
3. A bulky observation chamber is required and this causes physical lag.
4. The difficulty of observing the peak reading of a "live" meter.
5. Dependence on a "live" meter to indicate the true peak reading without undershoot or overshoot.
6. Dependence on exhause pipe diameter to establish sampling length.
7. Dependence on a single narrow light beam with the consequent ability of observing only a small proportion of the sample.
8. Dependence on an outside source of power for operation.
9. Requirement for compressed air or other secondary service.
10. Inability to scavenge with clean air to establish and check zero.
11. Inability to provide automatic correction for smoke temperature.
12. Multiplicity of settings and controls.
13. Lack of built-in, mid-scale, checking facility.

14. Lack of electrical filter with defined characteristic to eliminate "noise" without modifying the main smoke pulse shape.
15. Inability to "hold" the peak reading.
16. Inability to define accurately the physical sampling length.
17. Smoke sample density affected by ambient air movement (i.e., wind).

All the equipment at present available has one or more of these shortcomings. Meters available for acceleration testing generally provide a single light beam, the light and photocell being located in a frame adapted to fit on to the end of the exhaust pipe so that the light beam passes through the plume of exhaust gas as it issues from the pipe.

The present invention is concerned primarily, but not to the exclusion of steady state testing, with improvements in opacimeters for measuring the opacity of diesel engine exhaust emissions when measured by the free acceleration method, and according to the invention apparatus for measuring smoke density comprises a venturi passage through which smoke can pass, and a light source and at least one light-reflecting surface arranged in the vicinity of the passage to pass and reflect a light beam transversely through the throat of the venturi to form a V-shaped or multiple V-shaped beam.

Figure 2:
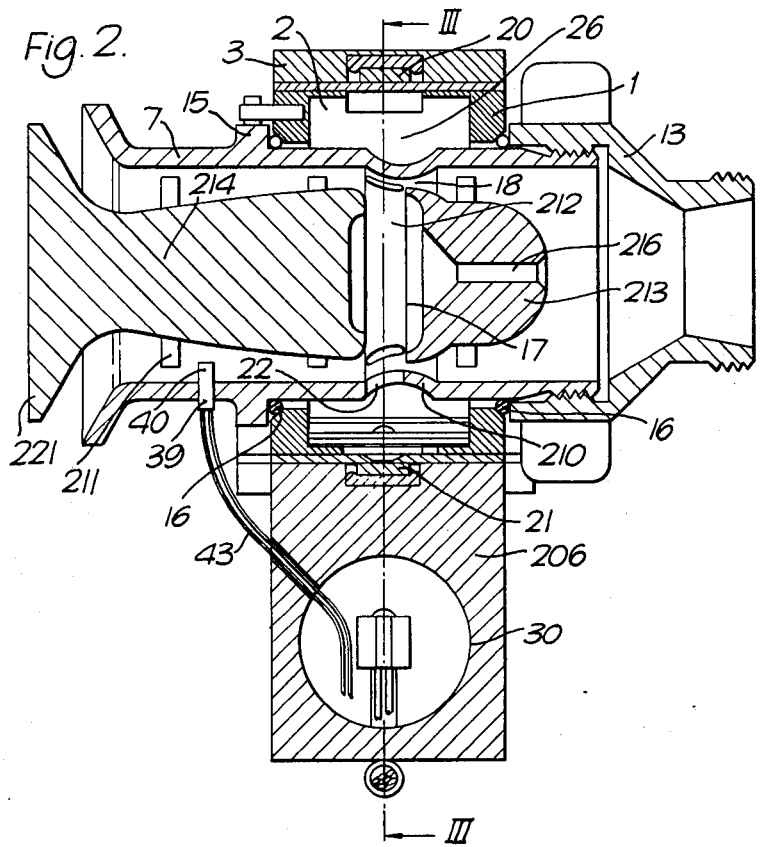
Figure 7:
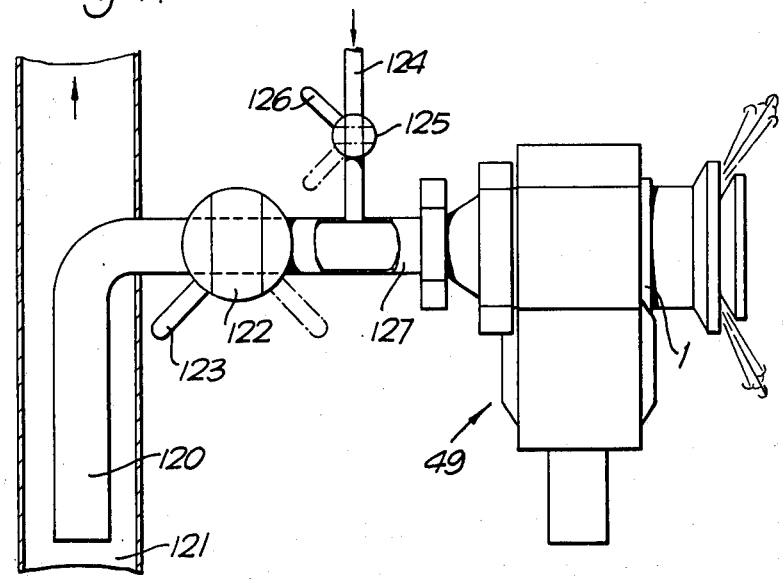
Figure 6:
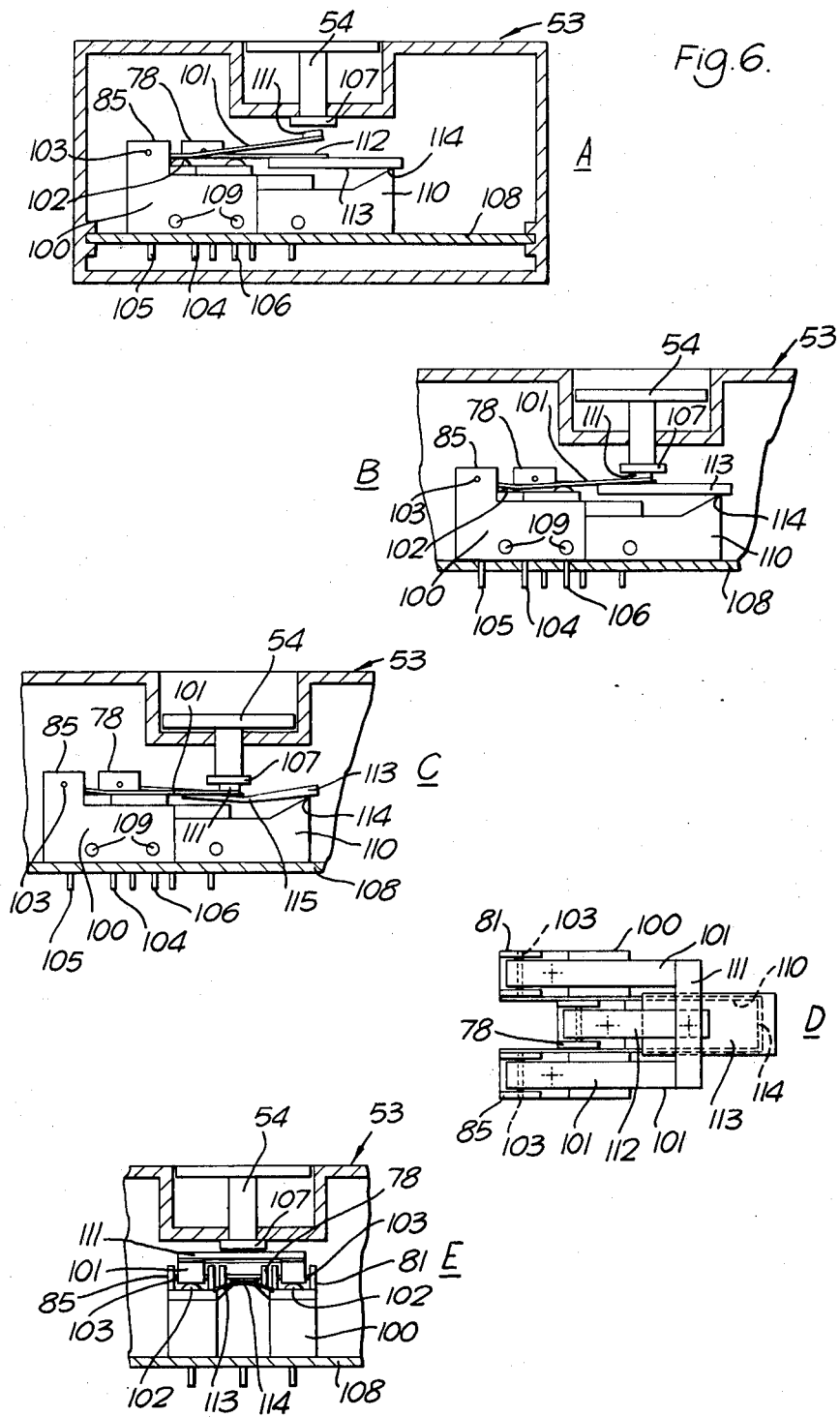

An example of apparatus in accordance with the invention is shown in the accompanying drawings, in which FIG. 1 is a view of the complete apparatus;
FIG. 2 is a section through the smoke head taken on the light II—II in FIG. 3;
FIG. 3 is a section through the smoke head taken on the line III—III in FIG. 2;
FIG. 4 shows the apparatus in use;
FIG. 5 is a block diagram of the electronic circuit within the display case showing also the signal shape at each of the various stages;
FIG. 6 shows five views A, B, C, D and E of the switch arrangement;
FIG. 7 shows the apparatus adapted for use in a test house;
FIG. 8 is an enlarged view of the handle shown in FIG. 1; and
FIG. 9 is a section through an alternative construction of the light path shown in FIG. 3.

As indicated above, FIG. 1 shows the complete apparatus with its probe 9 inserted into an exhaust pipe 50 of an engine (not shown), the probe being connected to a smoke head 49 by a bend 10 and two swivel nuts 11 and 12 so as to give complete articulation between the probe and the smoke head. A sample of the smoke passes up the probe and through the smoke head 49, issuing once more into the atmosphere at 63. A handle 200 on the end of an extension 201 serves (a) to insert the probe manually into the exhaust pipe when it is in an inaccessible position, and (b) to gain access to clean air which enters the handle 200 at holes 202.

The signal from a photocell 27 (see FIG. 3) passes through a multicore lead 36 to a hand-held display instrument 53. On depression of button 54, needle 60 displays on a display meter 56 the density of smoke 62 issuing from the exhaust pipe.

FIG. 4 shows an operator 203 using the apparatus on a vehicle 204 which is under the control of a driver 205. Operator 203 instructs the driver 205 by suitable manual signals when he wishes the driver to depress fully or release the accelerator of the vehicle 204.

FIGS. 2 and 3 show the smokehead 49 of the apparatus. It comprises a housing 1 which encloses a space 2 closed by a cover 3 retained by screws (not shown). The space 2 is also closed by a second housing 206 which itself contains two further housings 28 and 33. The housing 28 locates a light source 25 in holder 29, and the housing 28 is adjustably located by a grub screw 31. The housing 33 locates a photo-electric cell 27 and a thermister 35 together with a circuit board 34 containing suitable electronic amplifying equipment to stabilise the photo-cell signal output against temperature. The multicore lead 36 with its connection 37 contains sufficient conductors to supply current to the light source and amplifier and also to transmit the necessary signals back to the instrument 53. The housing 33 is adjustably located by a grub screw 32.

Within space 2 there passes a smoke tube 7 located by a flange 15 and a nut 13. 'O'-rings 16 thermally insulate the housing 1 from the hot smoke tube 7. The smoke tube has a waisted portion 210 which acts in conjunction with two internal plugs 213 and 214 located concentrically within the smoke tube by a number of radial struts 211 to form an annular venturi having its throat at 18. There are a number of radial holes 22 in the waisted portion 210 of the smoke tube for the passage of light from the light source 25. Two mirrors 20 and 21 are located to reflect the light from source 25 through the light holes 22 so as to form a 'W'-shaped beam of light 26 which, after passing four times transversely through the smoke tube and the space 212 between the plugs, ultimately falls on to the photo cell 27. The light beam may pass any number of times through the tube but it has been found that four times is preferable.

If desired, the space between the plugs through which the light passes can, to advantage, be replaced by four holes drilled along the four axes of the light beam (see FIG. 9). In this case the smoke feed hole 216 is deleted. This arrangement has the advantage that the two plugs 213 and 214 can be made in one piece and also, which is more important, light from the source 25 cannot reflect internally from particle to particle, and so cause some of the light to reach the cell without passing through the full length of the light path. This is important where the smoke contains water vapour or unburnt liquid fuel mist.

The hole 216 in the FIG. 2 construction serves to fill the space 212 with smoke, and the annular venturi, having a relatively small area, produces a depression at the inside ends of the light holes 22 considerably greater than would be possible without the plugs 214 and 215, whilst at the same time providing a relatively long path of light passing through the smoke sample.

Plates 217 and 218 (see FIG. 3) are provided with sharp-edged holes or "stops" 219 to orientate the light beam and prevent internal reflections. The plates also provide accurate location for the mirrors which are held against the outer surfaces of the plates by flexible pads 220.

When smoke passes through the venturi throat 18, it produces a reduction in pressure at the light holes 22 which causes clean air to be drawn through the passage 19 and handle extension 201 from holes 202 in the handle 200. This clean air forms an interface with the smoke at the inner ends of the light holes 22 and thus defines the total length of the smoke sample through which the light beam passes. The clean air also prevents pollution of the surfaces of the mirror and of the light source and photo cell.

A thermocouple component 39 attached to a thin blade 40 (see FIG. 2) is inserted through the wall of the smoke tube, and its conductors are incorporated within the multicore cable 36. This avoids the undesirable use of any form of electrical plug or other form of connector.

Flange 221 of the plug 214 serves to occlude ingress of ambient light which might otherwise gain access to the photo cell and it also shields the venturi from the direct effect of strong wind by preventing local stalling of the venturi.

A spindle 44 which is free to rotate in the plate 218 carries a knurled roller 45 and a disc or shutter 46 provided with a number of projections 47. The shutter 46 is located so that, when rotated by rolling a thumb across the roller 45, the projections each pass in turn through the light beam 26 so as to "chop" the beam. The angle subtended at the centre of spindle 44 by the two edges of each projection multiplied by the number of projections is arranged to be a predetermined percentage of 360° so that, when spinning, the shutter reduces the average light flux falling on the photo cell by a similar percentage. A magnet 48 attached to housing 206 is in close proximity to the shutter 46 so that, when not in use, the magnet attracts one of the projections 47 and holds the shutter in an angular position which does not obstruct the light beam.

The hand-held display instrument 53 includes a battery power source, electrical switches and electronic circuitry, as well as the display meter 56. The press-button 54 operates the electrical switches in two modes: (a) first pressure — half depressed, and (b) second pressure — fully depressed. The meter 56 has two scales, namely, a linear scale 57 graduated from 100 to 0 in Hartridge Smoke Units (H.S.U), and a non-linear scale 58 graduated from 00 to 0 in light-absorption coefficient units (K meters $^{-1}$). A light-emitting diode (LED) 59 lights up when the battery voltage falls below a value which might cause incorrect readings. The needle 60, when not in operation, lies at the left-hand end of the scale (at 100 H.S.U.). A knob 55 serves to set the needle to read zero prior to using the instrument. A cover 52 locates the batteries (not visible) within the case 53.

FIG. 5 illustrates an example of the preferred electronic circuitry of the apparatus. That part of the circuitry in the smoke head housing 1 is shown enclosed by the broken line 88, while that part in the display instrument 53 is shown enclosed by the broken line 89. The flexible multicored cable 36 and its plug and socket 36a (FIG. 1) connecting the two units together are shown at 87. The circuitry itself is shown in block diagram form for simplicity since the various functions are all well-known electronic practice. The operation is as follows:

Regulators 80 and 84 provide stable positive and negative lines, with respect to the zero volt centre tap line, for operating the system. A third regulator 79 provides a stable voltage for operating the light source 25. The said first pressure on the button 54 of the hand-held instrument 53 closes switches 81 and 85 and leaves switch 78 closed. On depression of the button 54, these regulated circuits are energised and the light source 25 lights.

The light from the source 25 passes to the photo cell 27 after following the path 26 through the smoke tube 7 of FIG. 2. The signal thereby produced passes to the head amplifier 67 which provides a signal of low source impedance to avoid interference picked up by the cable and plug connection 87 from stray external sources such as radio transmissions. The thermistor 35 maintains this signal constant for any one intensity of light flux should the temperature of the photo cell change in use. The initially-amplified signal is further amplified to more convenient proportions by preamplifier 70. A low-pass filter 71 passes signal frequencies below approximately 2Hz but substantially attenuates those above approximately 20Hz.

The smoothed signal now passes to log amplifier 72 where it is modified to a value equal to its logarithm. Index amplifier 73 now multiplies the signal value by a predetermined multiplier equal to the ratio: 430 (the smoke sample length which specifies the Hartridge Smoke Unit) divided by, say, 100 (which, for example, might be the combined length of that part of the light path 26 of FIG. 2 which passes through the smoke tube 7; that is to say, the smoke sample length). After multiplication, antilog amplifier 74 takes the antilogarithm so that, in effect, the signal strength has been raised to the power of 4.3. As already explained, percentage opacity smoke units dictate that the reading shall be 100 when no light penetrates the smoke and the signal is zero, the reading being zero when there is no smoke and the signal is positive. The meter 56, which the signal ultimately operates, is therefore scaled with the "at rest" extremity of the scale marked 100 and the full scale deflection extremity marked zero, the divisions and subdivisions being linear.

The peak and follow amplifier 76 detects and holds the highest signal strength reached and passes the "held" value to the meter 56. But the switch 77 (opened by the second pressure of the button 54) when closed resets — or cancels — the holding ability of the amplifier 76 so that, with switch 78 closed, the signal to the meter 56 continuously follows the variations of signal strength into the amplifier 76. It is necessary however to hold the highest reading on the meter which is in effect the lowest signal strength fed to the meter. It is therefore convenient to introduce the "times minus one" amplifier 75 which inverts the signal to negative, going instead of positive before it enters the peak and follow amplifier 76. The signal strength with no smoke will be at its maximum value, but, because of component tolerances and light path efficiency, the value cannot be specific. The zero set control 55 compensates for these variations and permits the meter to be set to read zero with no smoke present.

It has already been explained above how the components 72, 73 and 74 raise the incoming signal level to a power represented by the smoke sampling length specified for H.S.U. divided by the smoke sampling length for this invention. This function has three purposes, as follows:

1. It achieves a linear scale deflection for H.S.U. in order to conform with the linear scale of the Hartridge Smoke Meter (described in our prior British Pat. No. 918,525) which gave rise to the Hartridge Smoke Unit.
2. Omission of the scaling function would result in the centre portion of the scale being depressed towards zero so that the majority of readings taken from an engine would result in a very small meter pointer deflection due to the shorter and more convenient smoke sampling length adopted. This would result in poorer readability due, firstly, to smaller pointer deflection and, secondly, to the non-linearity of the scale itself.

3. Engine exhaust temperature at the tail pipe reaches a level sometimes in excess of 300° C. Furthermore, since the invention is primarily intended to operate over a short duration test mode, the actual temperature at the point of measurement of smoke density in the smoke tube 7 varies considerably and rapidly. Correction for temperature can be achieved by appropriately varying the gain of the index amplifier 73. Smoke particles distributed through exhaust gas follow the recognised gas expansion laws very closely and, therefore, to obtain the same signal output from the photo cell at a temperature of $x$ deg. C above that specified for H.S.U. (i.e. 100° C), one could increase the smoke sampling length by the ratio $$\frac{373 + x}{373}.$$

This is impractical, but the same effect will be obtained if the power to which the signal is raised is increased in the same proportion. That is:

$$\text{power} = \frac{430}{y \times \frac{373}{373} + x} = \frac{430 \times (373 + x)}{y \times 373}$$

where $x$ = smoke temperature in excess of 100° C, and
$y$ = smoke sampling length of the present invention in mm.

The meter 56 would normally also be scaled in Light Absorption Units (K).

The graphs of FIG. 5 show the signal shape at each stage. The final graph on the right-hand side of FIG. 5 shows how the meter reading relates to the light flux falling on the photo cell 27. It also shows the function of the zero set control 55 and the thermocouple 39. When the voltage drop across the regulator 79 falls below a predetermined minimum, the light-emitting diode 59 is switched on to indicate that the output of one or both of the batteries has fallen to an unacceptable level or the light 25 is not lit. The diode 65 by-passes the regulator 79 and the switch 81 in the reverse direction to permit a battery charger to be plugged into the instrument 53 at the connection 37 for charging the batteries 82 and 83.

FIG. 6 shows the switch arrangement whereby first and second pressures on the button 54 of the hand-held instrument 53 operate the equipment to display "continuous reading" and "peak and hold" modes. The switch mechanism makes use of three standard-pattern "micro switches" 78, 81 and 85, the mechanism having a body 100 and blades 101 pivoted at 103 which, when depressed, exert pressure on one or more plungers 102 and operate the switch mechanism. Relaxing the blade allows the switches to return to their original positions. The micro switches 78, 81 and 85 have three contacts 104 (common) 105 (normally open) and 106 (normally closed). It is therefore only necessary to "operate" the button 54 and select the appropriate contacts to achieve the desired switching function.

The button 54 is carried in a pocket in the instrument 53 and has a pad 107 at its inner extremity. Circuit board 108, located in the display case 53, carries the switch body 100. The micro switches 78, 81 and 85 have two holes 109 for location purposes. They are located in "V" formation so that only one of these holes in each switch is in register. A folded separator member 110, shown in broken line in plan view D, fits between the switches and is located by bolts (not shown) passing through holes 109. The blades 101 of the outer switches 81 and 85 are coupled together by a bridge piece 111. The blade 112 of the centre switch 78 carries an extension 113 of part-cylindrical section (see view E) and made of spring steel. This extension abuts the separator 110 at point 114.

When the button 54 is depressed, it bears on the bridge piece 111 and pushes down the twin blades 101 to operate the switches 81 and 85. Then the bridge 111 contacts the blade 112. The extension 113, being of semi-cylindrical section, offers considerable resistance and arrests the button 54 until greater pressure causes the extension 113 to collapse suddenly at point 115 (see View C of FIG. 6) where the blade 112 terminates. Under reduced resistance, the button 54 moves to the end of its travel and, in so doing, operates the centre switch 78. Relaxation of pressure on the button 54 permits the extension 113 to return the button to its centre position and the centre switch 78 to its original state. Further relaxation allows biassing springs (not shown) inside the switches 81 and 85 to return the button 54 to its uppermost position and these switches also return to their original state.

FIG. 7 shows how the smoke head 49 can be adapted for use in an engine test house for measuring "steady state" or "acceleration" smoke density with the engine under constant load. A probe 120 is fixed into the exhaust pipe 121 of the engine (not shown) so as to face upstream of the exhaust gas flow. A stop valve 122, operated by a handle 123, permits or prevents passage of exhaust gas to the smoke head 11. Compressed air, which is normally available in a test house, is connected to a pipe 124 and, with valve 122 closed, a valve 125, operated by a handle 126 can be used to admit compressed air which clears exhaust gas from the smoke head 1 and facilitates checking and setting the zero of the meter on the instrument 53 (not shown in FIG. 7) which can be located at a position convenient to the engine test engineer. Location of the smoke head 1 close to an air extractor fan (not shown) will prevent contamination of the test house with exhaust gas during the relatively short periods when the valve 122 is open for smoke measurement. For this purpose, a connecting pipe 127 may be of considerable length when reading smoke density under steady state conditions. But, if smoke is to be measured under acceleration conditions, the pipe 127 should be kept short to avoid denigrating the advantages of this invention for acceleration testing of smoke density.

FIG. 8 shows a sectioned detail of the handle 200. An internal valve 223 closes off communication between an internal bore 222 of the handle and holes 202 through which clean air can enter when the handle is held in a substantially vertical attitude with the smoke head on the ground, this being the natural attitude in which to hold the apparatus after withdrawal from the exhaust pipe. The purpose of the valve 223 is explained below.

After removal of the probe 9 from the exhaust pipe, it is necessary to recheck the zero setting. Ambient air currents soon purge the smoke tube and probe of residual smoke, but after this has happened the handle would act as a chimney, with the hot smoke tube at the bottom, and therefore convection currents of air would pass up the handle. Hot air passing through the light holes, in mixing with the cool air in space 2 of the smoke head, would cause a multiplicity of hot/cold interfaces, and these would refract the light beam and cause the needle 60 to fluctuate unpredictably. The valve 223 however prevents this happening by preventing air flow altogether as soon as the handle is held in a vertical attitude.

In order to fulfil the above function, the valve 223 is provided with two P.T.F.E 'O'-rings 224 and 225, these being a free fit inside the bore of the handle so that the valve 223 slides very freely. Seat 226 is located inside the bore of the handle so that an end face lies adjacent to the edges of the four holes 202. Spring 227 has one end located to valve 223 and the other attached to an abutment 228 axially adjustable within the bore of the handle and located by a screw at 229. Spring 227 has a low rate such that the weight of the valve will stretch it considerably. With the handle set to approximately 30° from vertical, abutment 228 is set so that valve 223 just touches the face of seat 226. When the apparatus is in use, handle 200 will be at a slope greater than 30° from vertical and the spring 227 will pull the valve open. But when it is desired to set zero, the handle will be held nominally vertical so that the weight of valve 223 causes it to shut.

Before the apparatus is used, the cable 36 of the smoke head 49 is plugged into the socket at 36a on the display instrument 53, and the button 54 pressed to first pressure. This illuminates the light source 25 which causes the meter 56 to show a reading. At this stage the smoke tube 7 will contain clean air only and the indicated reading should be zero. If it is not, the zero set control 55 is turned to obtain a zero reading. While retaining button 54 at first pressure, the shutter 46 is spun by rolling the thumb across the roller 45 to reduce the light flux falling on the photo cell, and a check is made that the reading on the meter 56 is correct. The "mark/space" ratio of the shutter can be arranged to simulate any desired smoke opacity at any temperature and may have, for example, five projections 47 each subtending an angle of 13° 22' at the centre.

This configuration gives a reduction in average light flux of 18.56 which, with a smoke sampling length of, for example, 100 mm, and a temperature of, say 20° C, would be equivalent to 50 H.S.U. as follows: 50 H.S.U. | 50% obscuration | 0.5 transmission factor
Smoke sampling length for H.S.U. = 430 mm and for the present apparatus = 100 mm.
Smoke temperature of H.S.U. = 100° C and for this check, say, 20° C.
Therefore, required shutter transmission factor is obtained from $y\sqrt{0.5}$
where $$y = \frac{430}{100 \times \frac{(273 + 100)}{(273 + 20)}} = \frac{430 \times 293}{100 \times 373} = 3.3778$$

whence transmission factor = 0.8144

And, projection angle for 5 projections =
$$\frac{(1 - 0.8144) \times 360}{5} = 13° 22'$$

This "shutter" filter, working as it does on fundamental principles, has considerable advantages over a transparent filter because of the difficulty of ensuring the absolute cleanliness which is essential in view of the very high transmission factor necessary and also the difficulty of defining the precise wave-length of the light source to which transparent filters are sensitive.

The nuts 11 and 12 are now slackened to permit the probe 9 (and the bend 10) to be swivelled into a convenient relationship to the smoke head 49. With the probe 9 inserted into the exhaust pipe of a running engine, a momentum of the gas induces a flow of a proportion of the gas through the probe, the bend 10, the nut 13 and the smoke tube 7 into the atmosphere. The gas, in passing through the throat 18 of the smoke tube 7, causes a local depression at holes 22 which causes clean air to pass up the hole 19 of the handle 200 into the enclosed space 2 whence it passes through the holes 22 and into the atmosphere with the exhaust gas. This clean air substantially prevents contamination of the glass surfaces 20, 21. It also contributes to the heat loss from the housing 1 and the electronic circuit 34.

The smoke, in flowing through the throat 18 of the venturi, passes through the four spaced-apart beams of light and, in so doing, reduces the flux falling on the photo cell. Because the plane of the light beams is at right angles to the direction of flow of smoke and also because there is a multiplicity of light beams, the smoke sample "seen" by the total light path 26 represents a substantial proportion of smoke. The physical response time is therefore very short and the proportion of smoke observed is considerably higher than would be the case with existing meters in which the light beam makes only one pass through the smoke sample. (Physical response time is defined as the time of transit of smoke through the light path). Both these factors are important criteria because, when making smoke measurements by the acceleration method, the smoke density quickly rises to a peak value and then immediately falls back, and also the distribution of smoke particles tends not to be entirely homogeneous.

Because the smoke passes through a venturi, the flow pattern is laminar and, therefore, smoke sample length at the throat 18 is well defined, and so also is the length of each of the four light beams passing through it. This facilitates an improvement in accuracy of the measurement of opacity. The flow of clean air through the holes 22 is small and does not penetrate into the smoke sample until it has passed downstream of the light beams.

When the smoke tube 7 contains clean air, the signal strength from the photo cell is at a maximum and is set manually to read zero on the meter 56 by adjusting the control knob 55. When smoke is introduced, the photo cell signal falls in proportion to the opacity of a sample of that smoke equal in length to the aggregate length of all those portions of the light beam 26 which fall within the confines of the venturi throat 18 (this is the sampling length). As has been explained already, the electronic circuit re-organises the photo cell signal and causes the meter to express the opacity linearly as a percentage in terms of what the percentage would be if the sampling length were 430 mm which is the basis of the Hartridge smoke meter.

The thermocouple 39, which is mounted on a thin blade, has a very low heat inertia and substantially records the transient temperature of the smoke and further modifies the photo cell signal (as has been explained) so as to correct the reading of opacity, as measured at its transient temperature, to what it would be at 100° C which is the base temperature of the Hartridge Smoke Unit.

After a period of use, the smoke tube 7 may be removed to gain access to the mirror surfaces 20 and 21 for cleaning. This is only necessary when the gain of a preamplifier 70 cannot be raised sufficiently by the zero set control 55 to achieve a zero reading.

In summary, the operating steps or instructions to be followed by an engineer using the apparatus would be somewhat as follows:

1. Orientate the probe 9 for insertion into the exhaust pipe.
2. Plug the cable 36 into the display instrument 53, press the button 54 to first pressure, and adjust the knob 55 to achieve a zero reading.
3. Take the smoke head 49 in the other hand and, with the button 54 still pressed to first pressure, roll the thumb over the roller 45 and check that the meter reads the predetermined mid-scale value.
4. With the engine in a warm condition and with the button 54 released, insert the probe 9 into the exhaust pipe and instruct the driver to press the accelerator fully and quickly until the engine reaches full speed and then release the accelerator until the engine idles.
5. Repeat step (4) three more times to clear the engine or lubricating oil smoke and to warm up the smoke head 49.
6. Immediately following step (5), press the button 54 to second pressure and have the driver accelerate the engine as in step (4). The meter 53 will now display and hold the peak smoke opacity reached during the accelerating mode.
7. Remember the reading in step (6) and then cancel it by releasing the button 54 to first pressure (or by completely releasing the button).
8. Repeat steps (6) and (7) twice more. The average of these three readings is the result. (Three readings are necessary to ensure that the engine has reached a stable repeatable condition. If not, further readings may be necessary.
9. Remove the probe 9 from the exhaust and hold the handle 200 in a vertical attitude. Press the button 54 to first pressure - the meter should again read zero. Check also that the battery state indicator 59 does not light.

If a driver is not available, an extension to the cable 36 may be used to enable the operator to sit in the driver's seat and press the accelerator pedal himself. The probe 9 should then be retained in the exhaust pipe by an assistant.

It will be seen that the apparatus described above avoids all the undesirable features of the apparatus and instruments used hitherto. It is simple and quick to use and includes a number of novel features aimed primarily to fulfil the particular requirements of acceleration testing of smoke opacity. Many of these features are equally valuable when the apparatus is used, for example, in an engine test house as illustrated in FIG. 7. Of particular importance are the following specific features all of which are contained in the apparatus shown in the accompanying drawings:

a. Using multiple light beams on a lateral axis.
b. Providing a defined smoke path length (as opposed to using the exhaust pipe itself) in conjunction with hand-held apparatus.
c. Using a venturi passage.
d. Using a scaling circuit (72, 73 and 74).
e. Using a thermocouple.
f. Providing a clean air system.
g. Providing a hand-operated shutter.
h. Using a single operating control button 54 having two pressure stages.
i. Providing a battery warning light.

I claim:

1. Apparatus for measuring smoke density comprising a probe for insertion into an exhaust gas pipe, a tube connected to the probe for the passage, through the tube, of smoke collected by the probe, a waisted portion of reduced diameter in the tube, plug means located concentrically within the tube to form therewith an annular venturi the throat of which lies at the said waisted portion of the tube, a plurality of holes in the waisted portion of the tube, a light source arranged outside the tube in the vicinity of the waisted portion thereof to pass a light beam along a first straight path into the tube through a first one of said holes in the waisted portion of the tube, transversely through the throat of the venturi, and then out of the tube through a second one of said holes in the waisted portion of the tube, at least one light-reflecting surface arranged outside the tube in the vicinity of the waisted portion thereof to receive the light beam after it has passed out of the tube and to reflect the light beam back into the tube along another straight path which does not coincide with any earlier path of the beam and through a corresponding one of the holes in the waisted portion of the tube, transversely through the throat of the venturi, and then out of the tube through yet another one of the holes in the waisted portion of the tube, a photo-electric cell positioned outside the tube in the vicinity of the waisted portion of the tube to receive the reflected light beam after it has passed out of the tube through a respective one of said holes, and visible display means connected to said photo-electric cell to receive an electrical signal therefrom whereby a visible display is given of the smoke density measured by the apparatus.

2. Apparatus according to claim 1, in which plates with sharp-edged holes are provided outside the tube between the light source and the tube, between each light-reflecting surface and the tube, and between the photo-electric cell and the tube, the said sharp-edged holes thus allowing the light beam to pass through the plates but preventing undesired reflections of the light beam.

3. Apparatus according to claim 1 having at least two light-reflecting mirror surfaces positioned outside the tube in the vicinity of its waisted portion but at different locations to reflect light beams reaching them through respective holes in the tube back into the tube.

4. Apparatus according to claim 3, in which the light source and the mirror surfaces are so disposed that a light beam from the light source passes four times through the venturi throat.

5. Apparatus according to claim 1, in which a clean-air passage is connected to the tube to permit the venturi to entrain clean air which thus forms an interface with smoke in the tube at the inner ends of the holes in the waisted portion of the tube and defines the boundary of the smoke sample through which the light beam passes.

6. Apparatus according to claim 5, in which the clean-air passage is formed in a handle of the apparatus and is controlled by a valve on the handle.

7. Apparatus according to claim 6, in which means are provided to close the valve automatically when the handle is held in a vertical position.

8. Apparatus according to claim 1 having an ambient light and wind occluder adjacent the light source and each light-reflecting surface.

9. Apparatus according to claim 1, in which the photoelectric cell is connected to an electronic circuit located close to the cell for amplifying and stabilising the electrical output from the cell.

10. Apparatus according to claim 9, in which the electronic circuit for amplifying and stabilising the electrical output from the cell is connected to electronic and electrical equipment comprising a log amplifier which amplifies the lower end of the smoke scale so as to cover in one scale the whole range of smoke densities met with in diesel engines.

11. Apparatus according to claim 10, in which the venturi passage has a smoke temperature sensor arranged to operate in conjunction with the log amplifier to correct the electrical output of the electronic and electrical equipment for smoke temperature.

12. Apparatus according to claim 1, in which temperature-sensing means are arranged close to the photoelectric cell for the purpose of stabilising the electrical output from the cell against temperature changes.

13. Apparatus according to claim 1, in which the visible display means are incorporated in an instrument containing a portable source of electrical power, switch means for bringing the apparatus into operation, and further switch means for displaying the peak reading of the visible display means.

14. Apparatus according to claim 13, in which the switch means and the further switch means are both under the control of a single press-button.

* * * * *